US008608794B2

(12) United States Patent  
Girton et al.

(10) Patent No.: US 8,608,794 B2  
(45) Date of Patent: Dec. 17, 2013

(54) FLEXIBLE STENT WITH IMPROVED AXIAL STRENGTH

(75) Inventors: Timothy S. Girton, Edina, MN (US); Daniel J. Gregorich, Plymouth, MN (US); Brent C. Gerberding, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 127 days.

(21) Appl. No.: 13/359,731

(22) Filed: Jan. 27, 2012

(65) Prior Publication Data

US 2012/0123524 A1 May 17, 2012

Related U.S. Application Data

(62) Division of application No. 10/321,044, filed on Dec. 16, 2002, now Pat. No. 8,105,373.

(51) Int. Cl.
*A61F 2/06* (2013.01)

(52) U.S. Cl.
USPC ........................................... 623/1.15

(58) Field of Classification Search
USPC ............................... 623/1.11–1.54
See application file for complete search history.

(56) References Cited

U.S. PATENT DOCUMENTS

| 4,655,771 A | 4/1987 | Wallsten |
|---|---|---|
| 4,733,665 A | 3/1988 | Palmaz |
| 5,061,275 A | 10/1991 | Wallsten |
| 5,091,205 A | 2/1992 | Fan |
| 5,135,536 A | 8/1992 | Hillstead |
| 5,366,504 A | 11/1994 | Andersen |
| 5,522,881 A | 6/1996 | Lentz |
| 5,628,782 A | 5/1997 | Myers |
| 5,632,771 A | 5/1997 | Boatman |
| 5,725,547 A | 3/1998 | Chuter |
| 5,755,770 A | 5/1998 | Ravenscroft |
| 5,766,238 A | 6/1998 | Lau |
| 5,814,063 A | 9/1998 | Freitag |
| 5,824,046 A | 10/1998 | Smith |
| 5,843,168 A | 12/1998 | Dang |
| 5,868,780 A | 2/1999 | Lashinski |
| 5,922,021 A | 7/1999 | Jang |
| 5,980,553 A | 11/1999 | Gray |
| 5,984,929 A | 11/1999 | Bashiri |
| 6,001,123 A | 12/1999 | Lau |
| 6,027,527 A | 2/2000 | Asano |
| 6,042,606 A | 3/2000 | Frantzen |
| 6,146,403 A | 11/2000 | StGermain |
| 6,168,619 B1 | 1/2001 | Dinh et al. |
| 6,190,406 B1 * | 2/2001 | Duerig et al. ............. 623/1.2 |
| 6,206,911 B1 | 3/2001 | Milo |
| 6,210,429 B1 | 4/2001 | Vardi et al. |

(Continued)

FOREIGN PATENT DOCUMENTS

| EP | 0800801 | 10/1997 |
|---|---|---|
| EP | 679372 | 7/1999 |
| EP | 1190685 | 3/2002 |

*Primary Examiner* — David Isabella
*Assistant Examiner* — Ann Schillinger
(74) *Attorney, Agent, or Firm* — Vidas, Arrett & Steinkraus, P.A.

(57) ABSTRACT

A stent comprises a generally cylindrical band having a pattern of alternating first and second struts, the first struts being wider than the second struts, the first and second struts being of substantially the same length.

12 Claims, 8 Drawing Sheets

(56) References Cited

U.S. PATENT DOCUMENTS

| | | | |
|---|---|---|---|
| 6,221,099 B1 | 4/2001 | Andersen | |
| 6,264,685 B1 | 7/2001 | Ahari | |
| 6,287,331 B1 | 9/2001 | Heath | |
| 6,287,336 B1 | 9/2001 | Globerman | |
| 6,290,721 B1 | 9/2001 | Heath | |
| 6,309,414 B1 | 10/2001 | Rolando et al. | |
| 6,312,459 B1 | 11/2001 | Huang et al. | |
| 6,315,791 B1 | 11/2001 | Gingras | |
| 6,325,825 B1 | 12/2001 | Kula et al. | |
| 6,325,826 B1 | 12/2001 | Vardi et al. | |
| 6,327,772 B1 | 12/2001 | Zadno-Azizi et al. | |
| 6,330,884 B1 | 12/2001 | Kim | |
| 6,331,189 B1 | 12/2001 | Wolinsky et al. | |
| 6,331,190 B1 | 12/2001 | Shokoohi | |
| 6,348,065 B1 | 2/2002 | Brown et al. | |
| 6,423,090 B1 * | 7/2002 | Hancock | 623/1.15 |
| 6,461,380 B1 | 10/2002 | Cox | |
| 6,551,351 B2 | 4/2003 | Smith et al. | |
| 6,558,415 B2 | 5/2003 | Thompson | |
| 6,602,282 B1 | 8/2003 | Yan | |
| 2001/0039447 A1 | 11/2001 | Pinchasik | |
| 2001/0044652 A1 | 11/2001 | Moore | |
| 2002/0107562 A1 | 8/2002 | Hart | |
| 2002/0116049 A1 | 8/2002 | Girton et al. | |
| 2003/0004567 A1 | 1/2003 | Boyle | |
| 2003/0018380 A1 | 1/2003 | Craig | |
| 2003/0055485 A1 * | 3/2003 | Lee et al. | 623/1.15 |
| 2003/0195606 A1 | 10/2003 | Davidson et al. | |

* cited by examiner

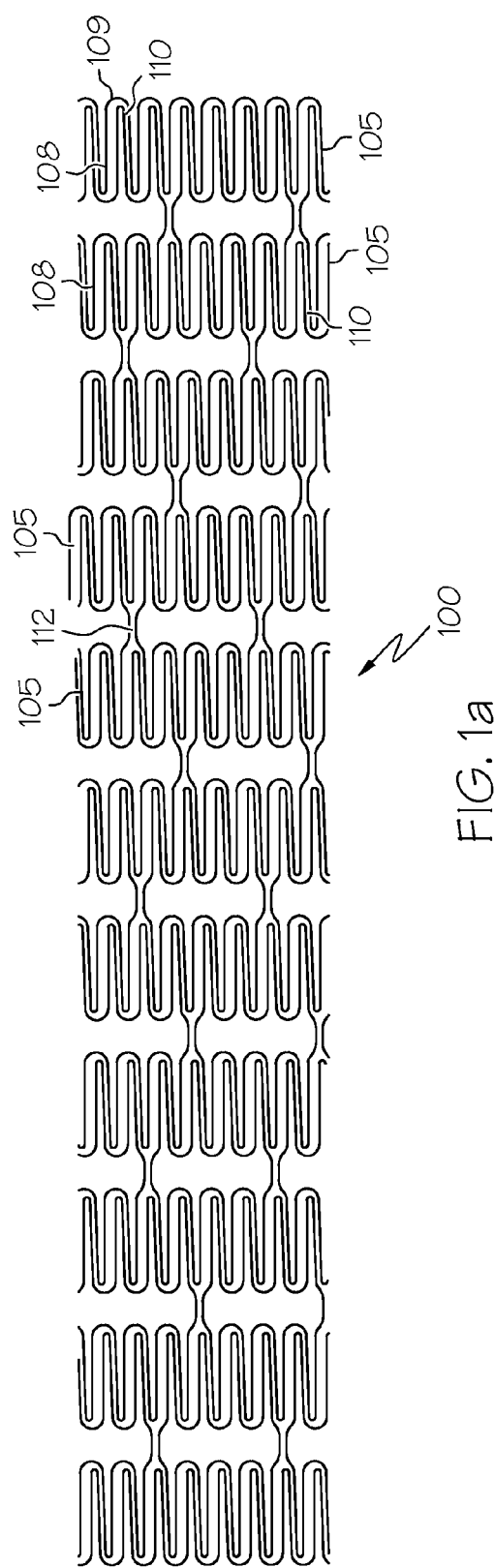

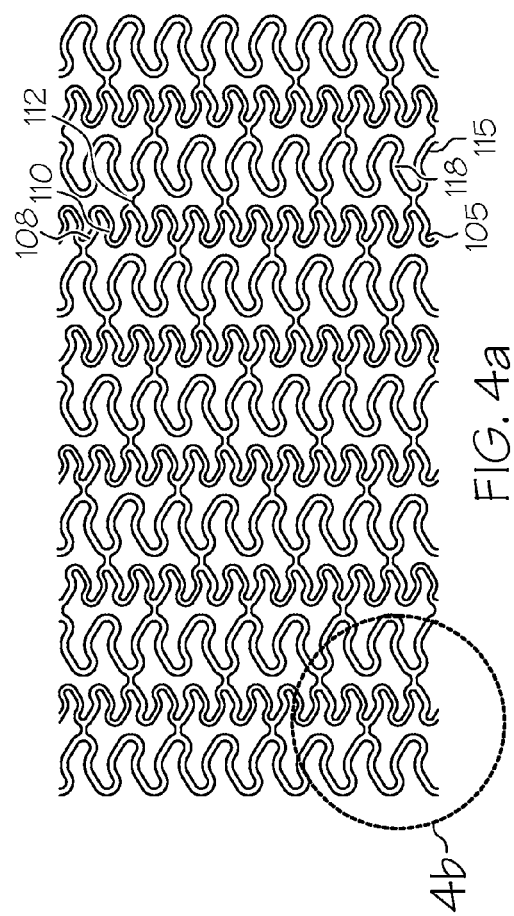
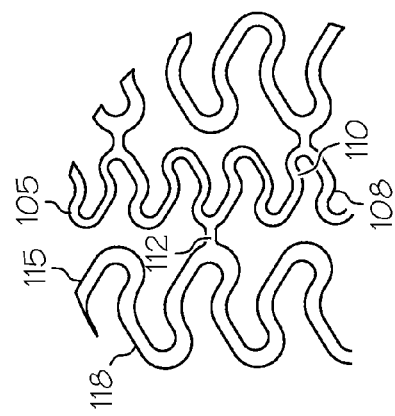
FIG. 4a
FIG. 4b

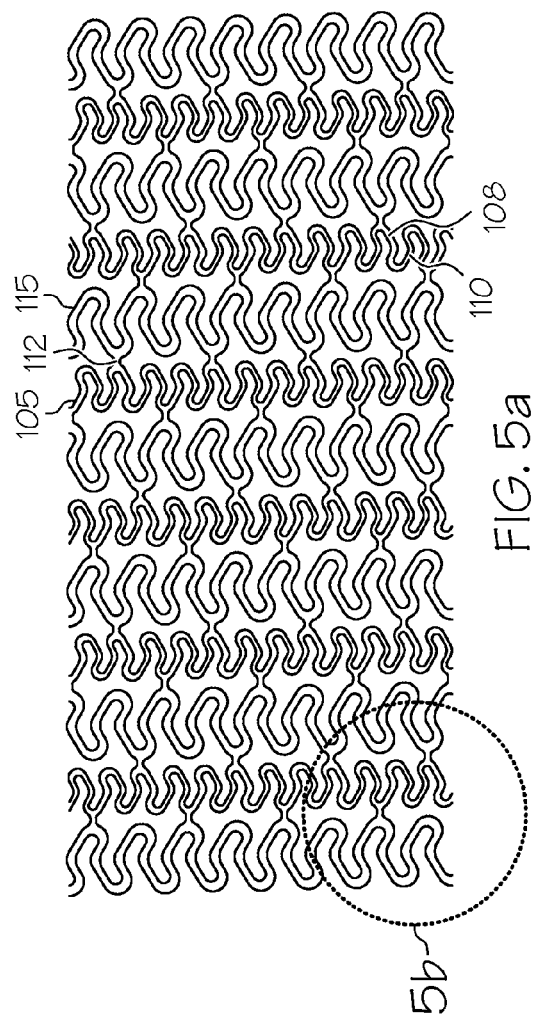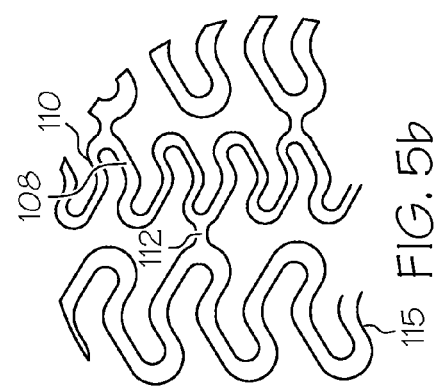

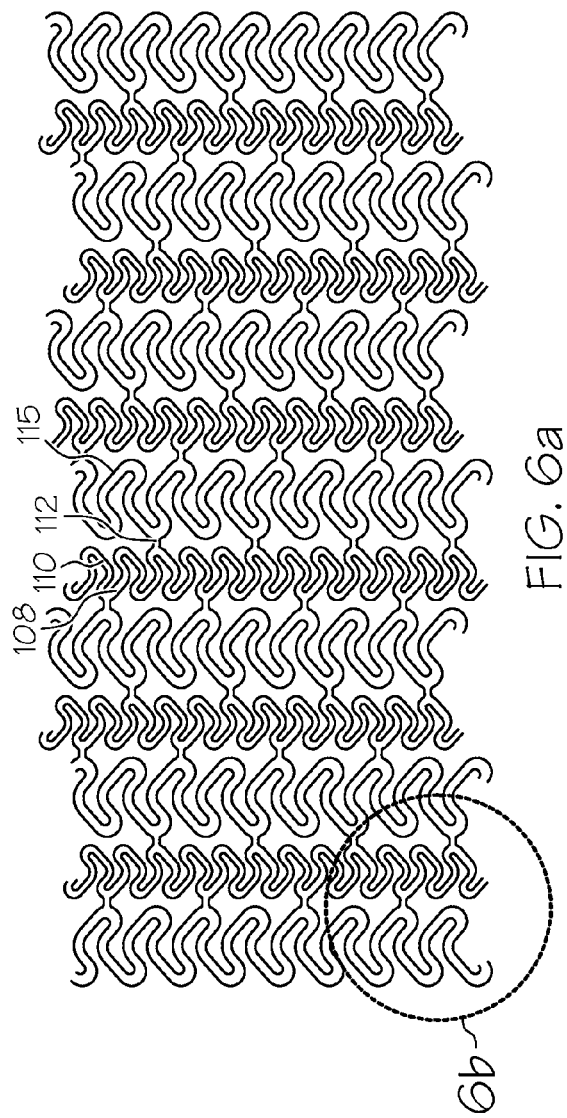
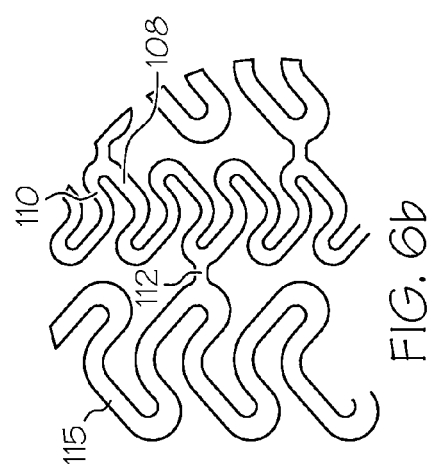
FIG. 6a
FIG. 6b

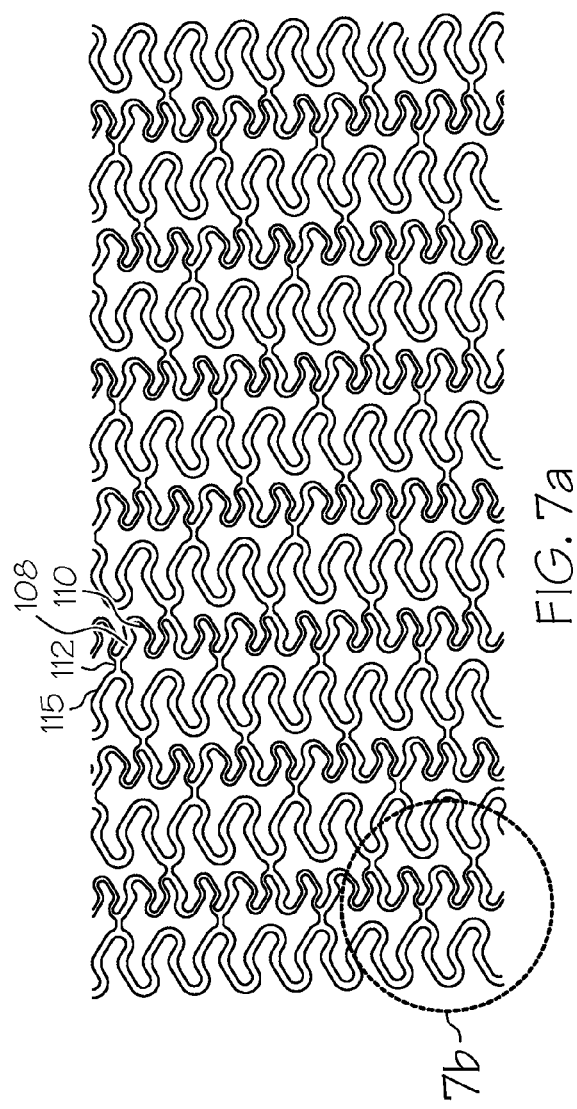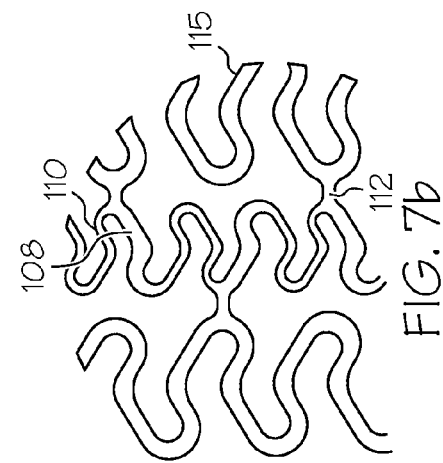

FLEXIBLE STENT WITH IMPROVED AXIAL STRENGTH

CROSS-REFERENCE TO RELATED APPLICATIONS

This application is a divisional application of application Ser. No. 10/321,044, filed Dec. 16, 2002, the entire contents of which is incorporated by reference.

BACKGROUND OF THE INVENTION

Stents are used in a wide array of bodily vessels including coronary arteries, renal arteries, peripheral arteries including iliac arteries, arteries of the neck and cerebral arteries as well as in other body structures, including but not limited to arteries, veins, biliary ducts, urethras, fallopian tubes, bronchial tubes, the trachea, the esophagus and the prostate.

Stents are typically balloon-expandable, self-expanding or a hybrid of the two. Balloon expandable stents may be made from a wide array of biocompatible materials including, for example, stainless steel. Self-expanding stents may also be made from a wide range of materials including biocompatible shape-memory materials including metals and polymers. An example of a suitable shape-memory metal is Nitinol.

In spite of the myriad of stent designs, there remains a need for novel stent designs as the technology of stent delivery progresses and as stents are employed with increasing prevalence in a variety of regions of the body.

As an example of the former, with the ever-increasing demand for stents to treat bodily vessels, there has been a demand for more flexible and trackable stents and stent delivery systems. One of the most significant recent changes to the stent delivery system involves the use of thin-walled balloons. This change has resulted in earlier cone deployment of the balloon which creates an inclined plane resulting in an inward axial force to the stent. The inward force, in turn, results in increased foreshortening of the stent upon deployment. Although a number of stents have been developed that are said to resist foreshortening, novel stent designs that generally resist foreshortening and in particular resist foreshortening when delivered on the newer thin walled balloons, are desirable.

As an example of the latter, in the area of aneurysm stenting, it is desirable for the stent to have relatively low radial strength to avoid dilating and rupturing the aneurysm. Standard techniques for reducing radial strength, however, typically result in stents which are not visible under fluoroscopy without the addition of radiopaque materials to the stent. The addition of radiopaque materials to the stent may alter the profile of the stent in the regions of the radiopaque material and may complicate the production of the stent. Thus, there is a need for novel aneurysm stents which are of low radial strength and which are visible under fluoroscopy.

All US patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

SUMMARY OF THE INVENTION

The invention, in one embodiment, is directed to a stent comprising a generally cylindrical band having a pattern of alternating first and second struts. The first struts are wider than the second struts and are of substantially the same length. Desirably, the first struts are at least twice as wide as the second struts. The struts may be straight or may include curved or bent sections.

Typically, the stent will comprise a plurality of the serpentine generally cylindrical band. Serpentine generally cylindrical bands which are adjacent one another are connected one to the other. Desirably, at least one and more desirably, all of the serpentine generally cylindrical bands are in the form of a closed cylinder.

The invention is also directed to a stent comprising a plurality of serpentine generally cylindrical bands where serpentine generally cylindrical bands which are adjacent one another are connected one to the other. At least one of the serpentine generally cylindrical bands is formed in a pattern of alternating first and second struts. The first struts are stronger than the second struts and are of substantially the same length. In one embodiment, the first struts have a greater width than the second struts. Desirably, the first struts are at least twice as wide as the second struts. In another embodiment, the first struts have a greater thickness than the second struts. Desirably, the first struts will have a greater resistance to radial deformation that the second struts. The first and second struts may be made of the same material or of a different material. Desirably, at least one and more desirably, all of the serpentine generally cylindrical bands are in the form of a closed cylinder.

The invention is also directed to a stent comprising a plurality of interconnected serpentine generally cylindrical bands. At least one of the bands is formed in a pattern of alternating first and second struts, the first and second struts extending in a substantially non-circumferential direction. The first struts are stronger than the second struts. The first and second struts may be of substantially the same length or of different lengths. In one embodiment, the first struts have a greater width than the second struts. Desirably, the first struts are at least twice as wide as the second struts. In another embodiment, the first struts have a greater thickness than the second struts. Desirably, the first struts will have a greater resistance to radial deformation that the second struts. The first and second struts may be made of the same material or of a different material. Desirably, at least one and more desirably, all of the serpentine generally cylindrical bands are in the form of a closed cylinder.

The stent may be constructed such that the first struts are of a substantially constant width and the second struts may be of a substantially constant width. The stent may also be constructed such that each of the first struts are of a varying width and each of the second struts are of a varying width, the average width of the first struts exceeding the average width of the second struts.

The invention is also directed to a stent comprising a plurality of interconnected serpentine generally cylindrical bands. At least one of the bands is formed in a pattern of alternating first and second struts, each first strut having an average width wider than the average width of each second strut. The first and second struts are of substantially the same length.

The invention is also directed to a stent comprising a plurality of serpentine generally cylindrical bands. Bands which are adjacent one another are connected one to the other. At least one of the bands is formed in a pattern of alternating first and second struts with each first strut having a first width and each second strut having a second width of no greater than about one-half of the first width. Desirably, the first width is at least 0.006" and the second width is about 0.003".

The invention is also directed to a stent comprising a serpentine, generally cylindrical band. The band has a plurality of turns with struts extending therebetween. The struts include wider struts and narrower struts and are arranged in a pattern of alternating widths. Typically, the stent will comprise a plurality of the cylindrical band. Cylindrical bands which are adjacent one another are connected one to the other. Desirably, each turn has a width which tapers toward a narrower strut.

Typically, the stent is constructed such that the orientation of the narrower struts relative to a longitudinal axis of the stent changes between an unexpanded state of the stent and an expanded state of the stent and the orientation of the wider struts relative to a longitudinal axis of the stent does not significantly change between an unexpanded state of the stent and an expanded state of the stent. The narrower struts may deform as the stent changes between an unexpanded state and an expanded state while the wider struts do not substantially deform between an unexpanded state and an expanded state.

The invention is also directed to a stent comprising a serpentine, generally cylindrical first band having a plurality of turns with struts extending therebetween. The struts include wider struts and narrower struts and are arranged in a regular pattern of one or more wider struts and one or more narrower struts. In one embodiment, the regular pattern consists of a wider strut adjacent to a narrower strut. In another embodiment, the regular pattern consists of a wider strut adjacent to a narrow strut with the narrow strut adjacent to another narrow strut.

Typically, the stent will comprise a plurality of the first band, first bands which are adjacent one another connected one to the other. In one embodiment, the adjacent first bands may be connected via straight or curved connectors. In another embodiment, second serpentine bands may be disposed between adjacent first bands. The first and second bands may be of different wavelengths and amplitudes. The struts may be straight or may have one or more bent or curved portions.

The invention is also directed to a stent comprising a plurality of serpentine bands extending about the circumference of the stent. Serpentine bands which are adjacent one another are connected one to the other. At least some of the serpentine bands have first and second struts, the second struts reorienting on expansion of the stent, the first struts not substantially reorienting on expansion of the stent.

The invention is also directed to a stent comprising a first, second and third serpentine substantially circumferential band. Each serpentine band has a plurality of interconnected struts. The second band is disposed between the first and third bands and connected to the first band via a plurality of first connections and the second band is connected to the third band via a plurality of second connections. At least three struts of the second band extend between first and second connections which are nearest one another. At least one of the at least three struts is wider than the other of the at least three struts. Desirably, three struts of the second band extend between first and second connections which are nearest one another, one of the three struts being wider than the other of the three struts. Even more desirably, the wider struts extend from a connection.

The connections may extend angularly or in a longitudinal direction. The struts may be straight or bent.

In one embodiment, the first and third serpentine bands each have a first number of turns and the second serpentine band has a second number of turns, the first number exceeding the second number. The first and third serpentine bands may be of greater longitudinal extent than the second serpentine band.

The inventive stents may be provided in a self-expanding configuration, in a balloon expandable configuration or in a hybrid configuration.

The inventive stents may be configured for placement in any suitable bodily vessel disclosed herein. Where the stent is configured for use in cerebral vessels, the struts will typically have lengths of between about 1 mm and 2 mm.

Additional details and/or embodiments of the invention are discussed below.

BRIEF DESCRIPTION OF DRAWINGS

FIG. 1a is a flat pattern of an inventive stent.
FIG. 4a is a flat pattern of an inventive stent.
FIG. 4b shows an enlarged view of region A of the stent shown in flat layout view in FIG. 4a.
FIG. 5a is a flat pattern of an inventive stent.
FIG. 5b shows an enlarged view of region A of the stent shown in flat layout view in FIG. 5a.
FIG. 6a is a flat pattern of an inventive stent.
FIG. 6b shows an enlarged view of region A of the stent shown in flat layout view in FIG. 6a.
FIG. 7a is a flat pattern of an inventive stent.
FIG. 7b shows an enlarged view of region A of the stent shown in flat layout view in FIG. 7a.

DETAILED DESCRIPTION OF THE INVENTION

Figure 1B:
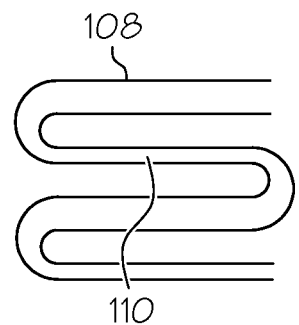
FIG. 1b shows several adjacent struts of the stent of FIG. 1 prior to expansion of the stent.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

Also for the purposes of this disclosure, the term 'bent strut' and the like does not implicate a method of manufacture and is intended to include struts which have curves, struts which are angled, and struts which are curvilinear, regardless of how the struts or the stent as a whole are manufactured.

Finally, for the purposes of this disclosure, points which are circumferentially aligned lie along a common line parallel to the longitudinal axis of the stent. Points which are longitudinally aligned lie along a common circumference.

In one embodiment, the invention is directed to a stent such as that shown generally at 100 in FIG. 1a comprising a generally cylindrical band 105 having a pattern of alternating first and second struts 108 and 110. The term 'generally cylindrical band' is intended to encompass both bands which extend all the way around the circumference of the stent as well as bands which extend most, but not all of the way, around the circumference of the stent. An example of the latter is a circumferential band which is missing one or more struts. First struts 108 are wider than second struts 110 and are of substantially the same length as the second struts 110. Desirably, first struts 108 are at least twice as wide as second struts 110, as shown in FIG. 1*a*. Circumferentially adjacent first and second struts are joined at one end of the struts only via turn 109. The width of the turn decreases from strut 108 to strut 110. In the embodiment of FIG. 1*a*, all of the generally cylindrical bands are provided with the alternating arrangement of wider and narrower struts.

In other embodiments of the invention, less than all of the bands have the alternating strut arrangement. For example, the stent of FIG. 1*a* may be modified such that one or more proximal and/or distal bands are provided with struts of uniform width.

Adjacent bands 105 are connected one to the other. Desirably, as shown in FIG. 1*a*, adjacent bands are connected via connectors 112. In the embodiment of FIG. 1*a*, two straight connectors 112 of a width intermediate the width of first strut 108 and second strut 110 connect adjacent bands 105. It is within the scope of the invention to provide wider or narrower connectors, longer or shorter connectors as well as more or fewer connectors between adjacent bands. Also, the connector may be curved have one or more bends and, optionally, one or more straight portions. The first and second ends of the connectors may be circumferentially aligned, as shown in FIG. 1 or may be circumferentially offset from one another.

As shown in FIG. 1*a*, it is desirable for the connectors to be arranged such that for each connector 112 extending from one end of a band, there is a connector 112 extending from the other end of the band which is separated from the other connector by three struts.

Figure 1C:
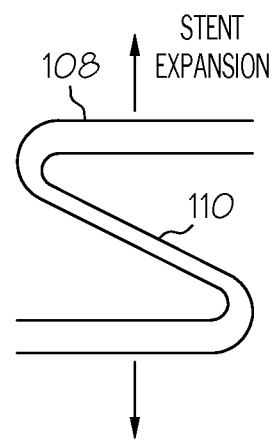
FIG. 1c shows the struts of FIG. 1b during expansion of the stent.

The stent of FIG. 1*a* is constructed such that the orientation of the narrower struts relative to a longitudinal axis of the stent changes between an unexpanded state of the stent and an expanded state of the stent and the orientation of the wider struts relative to a longitudinal axis of the stent does not significantly change between an unexpanded state of the stent and an expanded state of the stent. The narrower struts may deform as the stent changes between an unexpanded state and an expanded state while the wider struts do not substantially deform between an unexpanded state and an expanded state. FIGS. 1*b* and 1*c* show circumferentially adjacent wider and narrower struts before (FIG. 1*b*) and after (FIG. 1*c*) expansion of the stent. In FIG. 1*b*, struts 108 and 110 are parallel to the longitudinal axis of the stent. In FIG. 1*c*, wider struts 108 remain substantially parallel to the longitudinal axis of the stent while narrower struts 110 reorient relative to the longitudinal axis of the stent.

Without being bound by theory, it is believed that the wider struts provide axial rigidity and force transfer to points on the narrower struts that are not conducive to foreshortening.

Other embodiments of the invention are directed to stents having other arrangements of wider and narrower struts. In the embodiments of FIGS. 2-7, the struts are arranged in a repeating pattern of two narrow struts 110 and one wider strut 108. Each wider strut has two narrower struts on either side of it and each narrower strut has a narrower strut on one side of it and a wider strut on another side of it.

Figure 2:
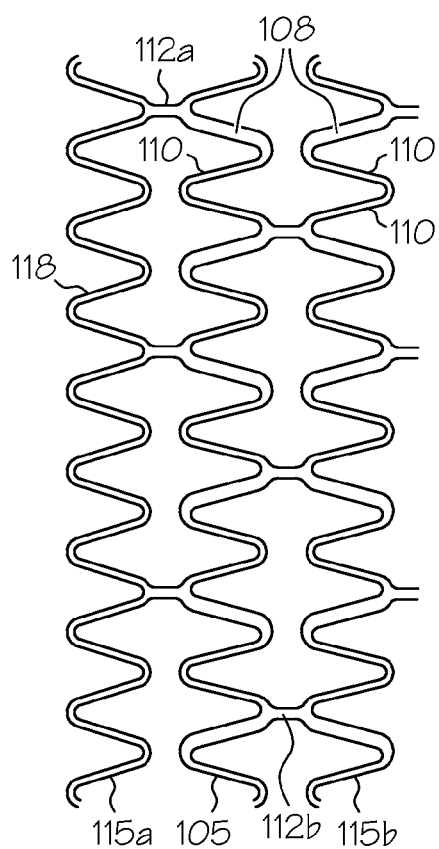
FIG. 2 is a flat pattern of an end of an inventive stent.
Figure 3:
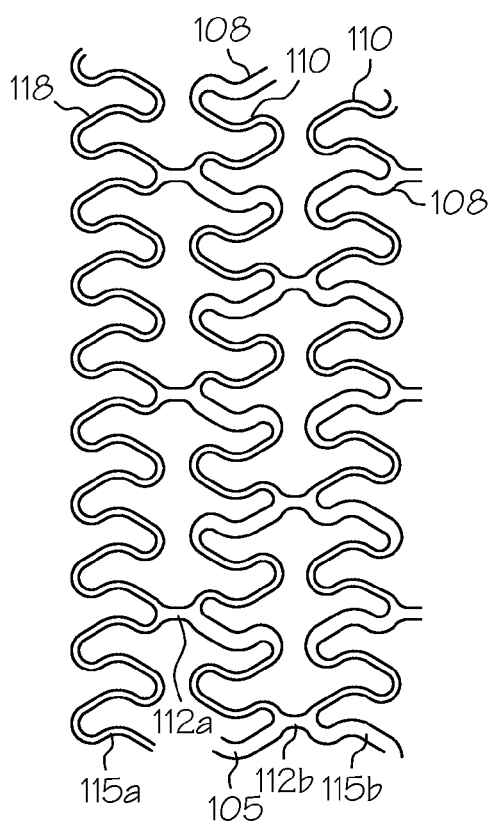
FIG. 3 is a flat pattern of an end of an inventive stent.

In the embodiment of FIGS. 2 and 3, one or both ends of the stent is provided with one circumferential band 115 with struts 118 of uniform width. The invention is also directed to embodiments in which a plurality of bands at one or both ends of the stent have uniform struts with the remainder of the stent having bands with the alternating arrangement of the struts. It is also within the scope of the invention for the stent to have alternating bands of struts of uniform width and bands of struts of non-uniform width as shown, by way of example, in FIGS. 4-7.

In the embodiment of FIG. 2, the struts are relatively straight. As shown in FIGS. 3-7, the inventive stents may also be provided with bent struts.

In the embodiments of FIGS. 4*a*-7*a* and 4*b*-7*b*, the stent is provided with first and second generally cylindrical bands 105 and 115 which alternate with one another along the length of the stent. The first generally cylindrical bands are of shorter longitudinal dimension than the second generally cylindrical bands and have more turns than the second generally cylindrical bands. Adjacent first and second generally cylindrical bands are connected one to the other at least one and desirably a plurality of connectors 112.

In the embodiment of FIGS. 4*a*-7*a* and 4*b*-7*b*, there are three bent struts extending between each connector 112 extending from one end of a first generally cylindrical band 105 and the nearest connector 105 thereto extending from the other end of the first generally cylindrical band. For every wider strut 108, there are two narrower struts 110 adjacent thereto.

The embodiments of FIGS. 4*a*-7*a* differ from one another in the ratio of the width of the wider strut to the narrower strut as well as in the angles of the struts relative to the longitudinal axis of the stent. Any of the stents shown in copending U.S. application Ser. No. 10/042,634, published as US 2002/0116049, may be modified in accordance with the instant invention.

Figure 8A:
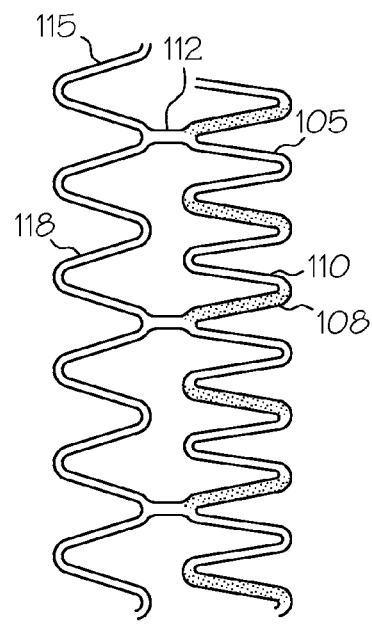
FIGS. 8a-8c show a flat pattern of a portion of another inventive stent along with its response to an axial force.
Figures 8B, 8C:
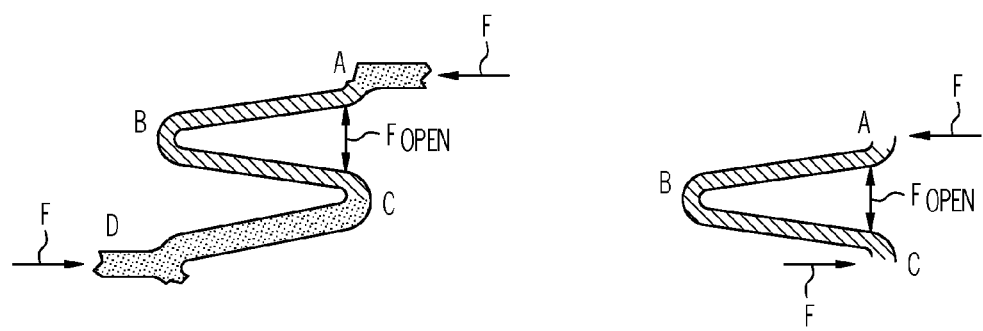

A portion of another inventive stent is shown in FIG. 8*a*. The stent includes alternating first bands 105 and second bands 115. First bands 105 include wider struts 108 and narrower struts 110. Struts 118 of second band 115 are of uniform width. Adjacent bands are connected one to the other via connectors 112. As shown in FIG. 8*b*, as an axial force F is transmitted along strut 108, it transfers its force from point D to point C, shown in FIG. 8*b*. As a result, joined struts 110 do not have the same freedom to shorten as they would otherwise have if strut 110 were narrower.

The invention is also directed to a stent comprising a plurality of serpentine generally cylindrical bands where serpentine generally cylindrical bands which are adjacent one another are connected one to the other and at least one of the serpentine generally cylindrical bands is formed in a pattern of first and second struts. The first struts are stronger than the second struts and are of substantially the same length. In one embodiment, the first struts have a greater width than the second struts. Desirably, the first struts are at least twice as wide as the second struts. An example of such a stent is shown in FIG. 1*a*. The first, stronger struts are shown at 108 and the second, weaker struts are shown at 110.

In another embodiment, not shown, the first struts are stronger in that they have a greater thickness than the second struts. Desirably, the first struts will have a greater resistance to radial deformation that the second struts. The first and second struts may be made of the same material or of a different material. Desirably, at least one and more desirably, all of the serpentine generally cylindrical bands are in the form of a closed cylinder.

In the various embodiments of the invention, disclosed herein, the first and second struts may be made of the same material or of different materials.

In some embodiments of the invention, as shown for example in FIG. 1, the stent may be constructed such that the first struts are of a substantially constant width and the second struts may are of a substantially constant width. In other embodiments of the invention, the stent may be constructed such that each of the first struts are of a varying width and each of the second struts are of a varying width, the average width of the first struts exceeding the average width of the second struts.

The invention is also directed to a stent, such as that shown in FIG. 1a, comprising a plurality of interconnected serpentine generally cylindrical bands. At least one of the bands is formed in a pattern of alternating first and second struts, each first strut having an average width wider than the average width of each second strut. The first and second struts are of substantially the same length.

The invention is also directed to a stent comprising a serpentine, generally cylindrical first band having a plurality of turns with struts extending therebetween. The struts include wider struts and narrower struts and are arranged in a regular pattern of one or more wider struts and one or more narrower struts. In one embodiment, the regular pattern consists of a wider strut adjacent to a narrower strut. In another embodiment, the regular pattern consists of a wider strut adjacent to a narrow strut with the narrow strut adjacent to another narrow strut.

Typically, the stent will comprise a plurality of the first band, first bands which are adjacent one another connected one to the other. The connection may be direct, via one or more straight or curved structures or may be indirect, in the case where a second serpentine band of another configuration is disposed between adjacent first serpentine bands. The first and second bands may be of different wavelengths and amplitudes.

The struts may be straight or may have one or more bent or curved portions.

The invention is also directed to a stent, such as that shown by way of example in FIGS. 2 and 3, comprising a first, second and third serpentine substantially circumferential band. Each serpentine band has a plurality of interconnected struts. Second band 105 is disposed between first and third bands 115a and 115b and connected to the first band via a plurality of first connections 112a and the second band is connected to the third band via a plurality of second connections 112b. At least three struts of the second band extend between first and second connections which are nearest one another. At least one of the at least three struts is a wider strut 108 than the other of the at least three struts 110. Desirably, three struts of the second band extend between first and second connections 112a and 112b which are nearest one another, one of the three struts being wider than the other of the three struts. Even more desirably, as shown in FIGS. 2 and 3, the wider struts 108 extend from a connection 112.

The connections may extend angularly or in a longitudinal direction. The struts may be straight or bent, as shown in FIGS. 2 and 3.

In one embodiment, the first and third serpentine bands each have a first number of turns and the second serpentine band has a second number of turns, the first number exceeding the second number. The first and third serpentine bands may be of greater longitudinal extent than the second serpentine band.

The inventive stents may be provided in a self-expanding configuration, in a balloon expandable configuration or in a hybrid configuration.

The inventive stents may be configured for placement in any suitable bodily vessel disclosed herein.

Where the stent is configured for use in cerebral vessels, the struts will typically have lengths of between about 1 mm and 2 mm. As a non-limiting example, the stent of FIG. 1a may be provided in an embodiment in which the struts are 1 mm to 2 mm in length or less. Such a stent, desirably self-expanding, would have at least some struts which are desirably thick enough and wide enough to be seen under fluoroscopy. As an example, where the stent has a wall thickness of approximately 0.003", the wider struts will desirably have a width of 0.0065" or more so that they may be viewed under fluoroscopy and the narrower struts, desirably, will be of no more than half the width of the wider struts and more desirably, approximately 0.003" or less. Desirably, as shown in FIG. 1, the turns between the wider struts and the narrower struts gradually tapers in width from the width of the wider struts to the width of the narrower struts. The stent may be provided in a range of diameters, depending on the diameter of the vessel in which it is to be inserted. Suitable diameters include 3 mm or smaller. The stent may also be provided in larger diameters as well. The stent may be used in stenting aneurysms. Suitable materials for such a stent include shape-memory materials such as Nitinol and spring-metal materials. Because it is desirable for self-expanding aneurysm stents to have reduced radial strength so as not to dilate the aneurysm, such stents will typically have reduced strut dimensions. The fat-skinny design of the stent of FIG. 1 not only allows for novel patterns of force transmission through the stent but also reduced radial strength as a result of the narrower struts along with reasonable radiopacity from the wider struts to maintain the radiopacity necessary to visualize the stent under fluoroscopy.

A stent such as that shown in FIG. 1 may be made of a shape-memory material such as Nitinol. In one embodiment, the stent pattern may be cut into a Nitinol tube and the tube expanded and heatset into shape using standard techniques for handling Nitinol. With such a stent, bending of the stent would occur mostly as a result of deformation of the thinner struts with the wider struts remaining largely undeformed.

Any of the inventive stents disclosed above may be provided with a uniform diameter or may taper in portions or along the entire length of the stent.

The invention is also directed to bifurcated stents. Any or all of the branches of a bifurcated stent and or the trunk may be provided with one or more generally cylindrical bands with wider and narrower struts as disclosed above.

The inventive stents may be manufactured using known stent manufacturing techniques including laser cutting, laser welding, chemically etching, electrode discharge machining or stamping a tube or a sheet. In the case of a sheet, the sheet is then rolled and welded. The inventive stents may also be molded with the desired design or may be made by growing or extruding or winding a stent with the inventive patterns. Further, the inventive stents may be assembled by providing individual generally cylindrical bands and connecting them together via welding or any other suitable joining technique.

Typically, in the case of stents which are laser cut from tubes or sheets, the laser cut tube or sheet will have to be polished using suitable polishing techniques as known in the art and cleaned using suitable cleaning techniques as known in the art.

Any suitable stent material may be used in the manufacture of the inventive stents. Examples of such materials include metals such as stainless steel, tantalum, elgiloy and shape memory metals such as nitinol, platinum/tungsten alloys and titanium alloys. The inventive stents may also be made of suitable polymeric materials.

The inventive stents may include suitable radiopaque coatings. For example, the stents may be coated with gold or other noble metals or sputtered with tantalum or the like. The stents may also be made directly from a radiopaque material to obviate the need for a radiopaque coating or may be made of a material having a radiopaque inner core. The entirety of the stent may include one or more radiopaque coatings or the radiopaque coatings may be limited to desired portions of the stent. In the case of the stent of FIG. 1a, although a radiopaque coating may be provided, the wider struts are typically configured to provide the stent with radiopacity.

The inventive stents may also be provided with various bio-compatible coatings to enhance various properties of the stent. For example, the inventive stents may be provided with lubricious coatings. The inventive stents may also be provided with drug-containing coatings which release drugs over time.

The coating may comprise one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anticoagulants such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms.

Genetic materials include anti-sense DNA and RNA, DNA coding for, anti-sense RNA, tRNA, or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cells can be of human origin (autologous or allogeneic) or from an animal source (xenogeneic), genetically engineered if desired to deliver proteins of interest at the transplant site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL®), fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

The inventive stents may also be used as the framework for a graft. Suitable coverings include nylon, collagen, PTFE and expanded PTFE, polyethylene terephthalate and KEVLAR, or any of the materials disclosed in U.S. Pat. Nos. 5,824,046 and 5,755,770. More generally, any known graft material may be used including synthetic polymers such as polyethylene, polypropylene, polyurethane, polyglycolic acid, polyesters, polyamides, their mixtures, blends and copolymers.

The inventive stents may be configured for use in a wide array of bodily vessels including coronary arteries, renal arteries, peripheral arteries including iliac arteries, arteries of the neck and cerebral arteries as well as in other body structures, including but not limited to arteries, veins, biliary ducts, urethras, fallopian tubes, bronchial tubes, the trachea, the esophagus and the prostate.

In addition to the specific embodiments claimed below, the invention is also directed to other embodiments having any other possible combination of the dependent features claimed below. As such, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 1; claim 4 may be taken as alternatively dependent on claim 3, or on claim 1; claim 5 may be taken as alternatively dependent from any of claims 1-4, etc.).

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A stent comprising:
    struts, the struts comprising:
        first struts each having a first width; and
        second struts each having a second width greater than the first width;
    turns, each turn engaging two struts, and each strut extending between two turns;
    the struts and the turns forming first serpentine bands, each first serpentine band including first struts and second struts; and
    connectors engaging some but not all the turns of adjacent first serpentine bands;
    wherein the second struts extend only from turns engaged to connectors and two second struts extend from each connector.

2. The stent of claim 1, wherein the connector is positioned between the two second struts.

3. The stent of claim 2, further wherein two first struts extend from each connector, and the connector is positioned between the two first struts.

4. The stent of claim 1, wherein each connector has a third width greater than the first width.

5. The stent of claim 1, wherein the connectors are straight.

6. The stent of claim 1, wherein the first and second struts are straight.

7. The stent of claim 1, wherein each connector has circumferentially offset ends.

8. A stent comprising:
    a plurality of struts comprising:
        first struts each having a first width; and
        second struts each having a second width greater than the first width;
    a plurality of turns, each turn engaging two of the plurality of struts, and each strut extending between two turns;
    the plurality of struts and the plurality of turns forming serpentine bands;
    a plurality of connectors engaging some but not all the turns of adjacent serpentine bands;
    wherein second struts are engaged only to turns engaged to connectors.

9. The stent of claim 8, wherein the connector is positioned between the two second struts.

10. The stent of claim 9, further wherein two first struts extend from each connector, and the connector is between the two first struts.

11. The stent of claim 8, wherein each connector has a third width greater than the first width.

12. The stent of claim 8, each connector has circumferentially offset ends.

* * * * *